(12) United States Patent
Kim et al.

(10) Patent No.: US 12,603,175 B2
(45) Date of Patent: Apr. 14, 2026

(54) METHOD AND APPARATUS FOR DETERMINING DIAGNOSIS RESULT DATA

(71) Applicant: KOREA UNIVERSITY RESEARCH AND BUSINESS FOUNDATION, Seoul (KR)

(72) Inventors: Jae Young Kim, Seoul (KR); Yoo Sang Baek, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 632 days.

(21) Appl. No.: 17/906,054

(22) PCT Filed: Mar. 23, 2021

(86) PCT No.: PCT/KR2021/003557
§ 371 (c)(1),
(2) Date: Jul. 14, 2023

(87) PCT Pub. No.: WO2021/182936
PCT Pub. Date: Sep. 16, 2021

(65) Prior Publication Data
US 2024/0412864 A1      Dec. 12, 2024

(30) Foreign Application Priority Data
Mar. 11, 2020      (KR) .......................... 1020200030275

(51) Int. Cl.
*G16H 50/20* (2018.01)
*G06T 7/00* (2017.01)
(Continued)

(52) U.S. Cl.
CPC ........... *G16H 50/20* (2018.01); *G06T 7/0016* (2013.01); *G16H 30/20* (2018.01); *G16H 30/40* (2018.01);
(Continued)

(58) Field of Classification Search
CPC . A61B 5/01; A61B 5/483; A61B 2018/00452; A61B 2562/0271;
(Continued)

(56) References Cited

U.S. PATENT DOCUMENTS 4,428,382 A      1/1984  Walsall et al.
8,078,262 B2 *   12/2011  Murphy ................. A61B 5/418
                                              600/478

(Continued)

FOREIGN PATENT DOCUMENTS

JP            3005540 B1     1/2000
JP        2008500113 A       1/2008
(Continued)

*Primary Examiner* — Courtney Joan Nelson
(74) *Attorney, Agent, or Firm* — HOLZER PATEL DRENNAN

(57) ABSTRACT

Disclosed is a method and apparatus for determining diagnosis result data by using a thermal image. A method for determining diagnosis result data may comprise the steps of: acquiring a first thermal image indicating a temperature change of skin, to which thermal stimulation has been applied, over time; acquiring a second thermal image indicating a temperature change of skin, to which cold stimulation has been applied, over time; extracting a temperature restoration feature of the skin from each of the first thermal image and the second thermal image; and determining diagnosis result data related to the skin on the basis of the temperature restoration feature extracted from the first thermal image and the temperature restoration feature extracted from the second thermal image.

11 Claims, 7 Drawing Sheets

(51) Int. Cl.
_G16H 30/20_ (2018.01)
_G16H 30/40_ (2018.01)
_G16H 50/30_ (2018.01)

(52) U.S. Cl.
CPC ... _G16H 50/30_ (2018.01); _G06T 2207/10048_
(2013.01); _G06T 2207/30088_ (2013.01)

(58) Field of Classification Search
CPC ........ A61B 5/015; G16H 50/30; G16H 50/20;
G16H 30/20; G16H 30/40; G06T 7/0016;
G06T 2207/10048; G06T 2207/30088
See application file for complete search history.

(56) References Cited

U.S. PATENT DOCUMENTS

| | | | | |
|---|---|---|---|---|
| 2011/0230942 | A1* | 9/2011 | Herman ................. | A61B 5/015 |
| | | | | 607/96 |
| 2017/0027450 | A1* | 2/2017 | Toledano .............. | G16H 50/20 |
| 2019/0328238 | A1* | 10/2019 | Achilefu ................ | A61B 5/015 |

FOREIGN PATENT DOCUMENTS

| | | |
|---|---|---|
| KR | 1020060012649 | 2/2006 |
| KR | 1020110042463 | 4/2011 |
| KR | 101479415 B1 | 1/2015 |
| KR | 1020150117071 | 10/2015 |
| KR | 101854246 B1 | 5/2018 |
| KR | 1020190084551 | 7/2019 |

* cited by examiner

110

120

130

METHOD AND APPARATUS FOR DETERMINING DIAGNOSIS RESULT DATA

TECHNICAL FIELD

The following description relates to a technique of determining diagnosis result data by using a thermal image and a technique for obtaining the thermal image.

BACKGROUND ART

A non-invasive diagnostic method has been sought after in an early diagnosis of a disease. Recently, there has been an attempt to apply a non-invasive diagnostic method based on thermal imaging to a medical field, based on the characteristics that all objects have a temperature greater than or equal to an absolute temperature and radiate heat energy corresponding to the temperature. Thermal imaging is an imaging technique for measuring and analyzing the amount of infrared radiation emitted from an object.

A malignant lesion shows pathologies, such as cell proliferation, an increased basal metabolism, an increased blood flow rate, and has a thermal imaging pattern that is different from normal tissue. For example, in a thermal image, a malignant melanoma is checked to have a higher temperature than that of a normal lesion. With this knowledge, research into comparing the malignant melanoma with the normal lesion is actively conducted in the dermatology field. However, a technique for measuring a subtle temperature change of a lesion is lacked in prior arts, and thus, the characteristic of the malignant melanoma having a higher temperature than that of a normal lesion has not been actively used in an actual clinical setting.

DISCLOSURE OF THE INVENTION

Technical Solutions

According to an aspect, there is provided a method of determining diagnosis result data by using a thermal image that includes obtaining a first thermal image representing a temperature change, over time, of skin to which heat stimulation is applied; obtaining a second thermal image representing a temperature change, over time, of skin to which cold stimulation is applied; extracting a temperature restoration feature of the skin from each of the first thermal image and the second thermal image; and determining diagnosis result data related to the skin, based on the temperature restoration feature extracted from the first thermal image and the temperature restoration feature extracted from the second thermal image.

The extracting the temperature restoration feature may include calculating temperature change rate values by each image frame from the first thermal image and determining an average value of the temperature change rate values to be a first temperature restoration feature.

The extracting the temperature restoration feature may include calculating temperature change rate values by each image frame from the second thermal image and determining an average value of the temperature change rate values to be a second temperature restoration feature.

The determining the diagnosis result data may include, when the temperature restoration feature is greater than or equal to a threshold value, determining a diagnosis target related to the skin to have an abnormality.

The determining the diagnosis result data may include, when the temperature restoration feature is greater than or equal to a threshold value, determining a diagnosis target related to the skin to have a vascular disease.

According to another aspect, a device for obtaining a thermal image for determining diagnosis result data includes a temperature controller for transmitting, to a probe, a control signal for applying heat stimulation and cold stimulation to skin; the probe for applying heat stimulation and cold stimulation to skin, based on the control signal of the temperature controller; a thermal image obtainer for obtaining a first thermal image from skin to which heat stimulation is applied by the probe and for obtaining a second thermal image from skin to which cold stimulation is applied by the probe; and a diagnosis result data determiner for determining diagnosis result data, based on the first thermal image and the second thermal image collected by the thermal image obtainer.

According to another aspect, a device for determining diagnosis result data by using a thermal image includes a thermal image receiver for receiving a first thermal image and a second thermal image from an apparatus for obtaining a thermal image; a temperature restoration feature extractor for extracting a temperature restoration feature of skin from each of the first thermal image and the second thermal image; and a determiner for determining diagnosis result data related to the skin, based on the temperature restoration feature extracted from the first thermal image and the temperature restoration feature extracted from the second thermal image.

The temperature restoration feature extractor may calculate temperature change rate values by each image frame from the first thermal image and determine an average value of the temperature change rate values to be a first temperature restoration feature.

The temperature restoration feature extractor may calculate temperature change rate values by each image frame from the second thermal image and determine an average value of the temperature change rate values to be a second temperature restoration feature.

The determiner may, when the temperature restoration feature is greater than or equal to a threshold value, determine a diagnosis target related to the skin to have an abnormality.

The determiner may, when the temperature restoration feature is greater than or equal to a threshold value, determine a diagnosis target related to the skin to have a vascular disease.

Effects

According to an example embodiment, measuring a subtle temperature change of a body may enable an early diagnosis of a disease.

According to an example embodiment, measuring a subtle temperature change of a body may enable accurate detection of a position of a lesion and may improve the accuracy of a disease diagnosis.

According to an example embodiment, a method, which may be used as an auxiliary system for diagnosing and treating a disease, may improve the quality of medical service.

According to an example embodiment, a system including a hardware part and a software part may be provided, in which the hardware part includes a high-resolution thermal image microscope part and an external stimulus (e.g., a heating probe and a cooling probe) and the software part is configured to measure a temperature change rate of a minute lesion part of a captured image.

According to an example embodiment, a subtle temperature change in a minute lesion may be measured.

According to an example embodiment, a disease diagnosis and a disease severity evaluation may be quantified.

According to an example embodiment, a device for monitoring a patient's condition may be provided for telemedicine through a method of measuring a subtle temperature change in a minute lesion and diagnosing a disease, based on a temperature change.

BEST MODE FOR CARRYING OUT THE INVENTION

Figure 1A:
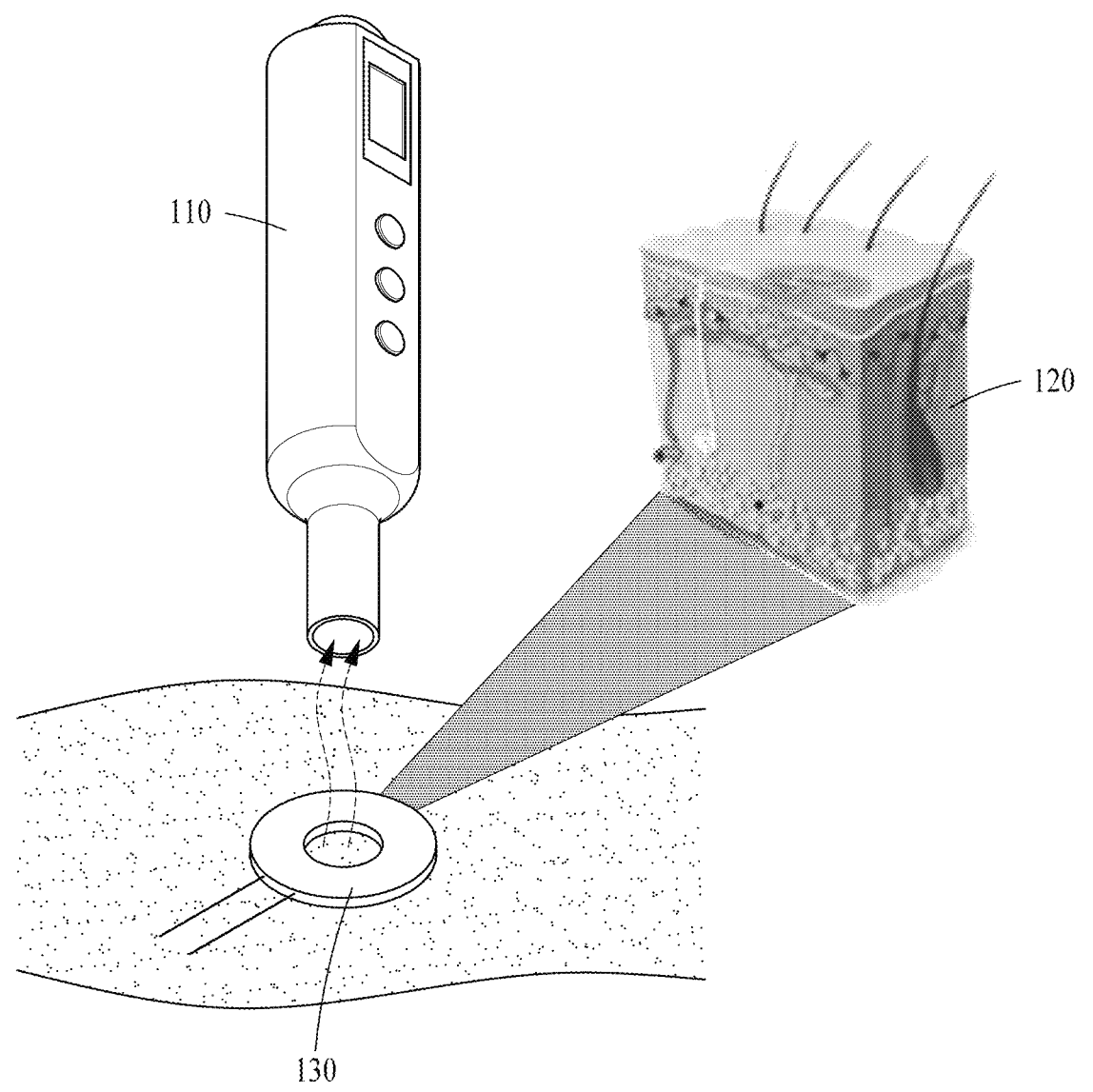
FIGS. 1A and 1B are diagrams each illustrating a device for obtaining a thermal image, according to an example embodiment.

Hereinafter, example embodiments will be described in detail with reference to the accompanying drawings. However, various alterations and modifications may be made to the example embodiments. Here, the example embodiments are not construed as limited to the disclosure. The example embodiments should be understood to include all changes, equivalents, and replacements within the idea and the technical scope of the disclosure.

The terminology used herein is for the purpose of describing particular example embodiments only and is not to be limiting of the example embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the example embodiments with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous interpretation of the present disclosure.

The example embodiments described herein may provide a technique for estimating a disease diagnosis result by analyzing a skin temperature restoration feature when each of heat stimulation and cold stimulation is applied to skin. A device for determining diagnosis result data by using a thermal image to be described below may extract a feature that skin restores from heat stimulation and cold stimulation, based on thermal images collected from the skin to which the heat stimulation and the cold 20 stimulation have been applied. The device for determining diagnosis result data may determine diagnosis result data on the skin included in the thermal images, based on the feature that the skin restores from the heat stimulation and the cold stimulation. The device for determining diagnosis result data may detect a malignant lesion or another lesion (e.g., an actinic keratosis) in contrast to normal tissue by sensing a subtle temperature change of the skin, based on the thermal images. The malignant lesion may include, for example, malignant melanoma, skin cancer, basal cancer, and the like. The malignant lesion has a higher temperature than that of surrounding normal lesions, and thus, whether there is a malignant lesion may be effectively distinguished through the thermal images.

Figure 1B:
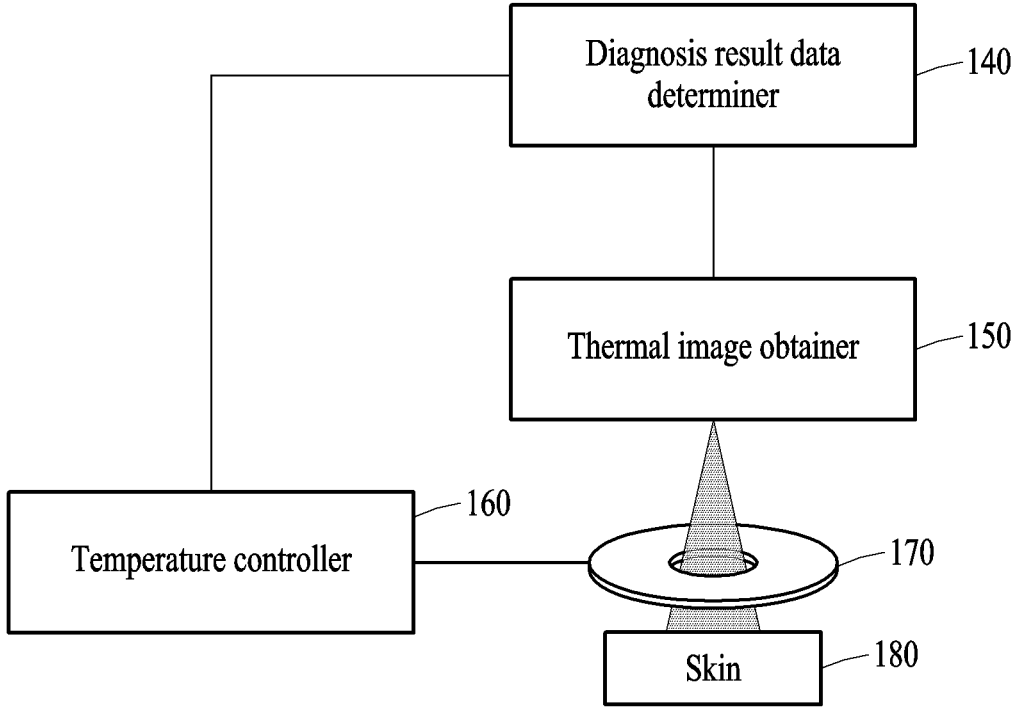

FIGS. 1A and 1B are diagrams each illustrating a device for obtaining a thermal image, according to an example embodiment.

Referring to FIGS. 1A and 1B, the device for obtaining a thermal image may include a temperature controller 160, probes 130 and 170, thermal image obtainers 110 and 150, and a diagnosis result data determiner 140.

The temperature controller 160 may transmit, to the probes 130 and 170, a control signal for applying heat stimulation and cold stimulation to skin 120 and skin 180. The probes 130 and 170 may apply heat stimulation and/or cold stimulation to the skin 120 and the skin 180, based on a control signal of the temperature controller 160. According to example embodiments, a thermal image obtainer may include one or two probes. When the thermal image obtainer includes one probe, the probe may apply both heat stimulation and cold stimulation. When the thermal image obtainer includes two probes, one probe may apply heat stimulation and the other probe may apply cold stimulation. The probes 130 and 170 may be of, for example, a ceramic material and may contact the skin 120 and the skin 180 and apply one of heat stimulation and cold stimulation to the skin 120 and the skin 180.

The thermal image obtainers 110 and 150 may obtain a first thermal image from the skin 120 and the skin 180 to which heat stimulation is applied by the probes 130 and 170 and may obtain a second thermal image from the skin 120 and the skin 180 to which cold stimulation is applied by the probes 130 and 170. In an example embodiment, the thermal image obtainers 110 and 150 may obtain a thermal image through an infrared camera. In example embodiments, the thermal image obtainers 110 and 150, as a temperature measurer, may measure a temperature change while obtaining a thermal image of the skin 120 and the skin 180 to which heat stimulation and cold stimulation are applied.

The diagnosis result data determiner 140 may determine diagnosis result data, based on the first thermal image and the second thermal image collected by the thermal image obtainers 110 and 150. The diagnosis result data determiner 140 may be, for example, one of a computer, a smart terminal, and a device for analyzing a skin temperature measurement graph extracted from an infrared camera.

Figure 2:
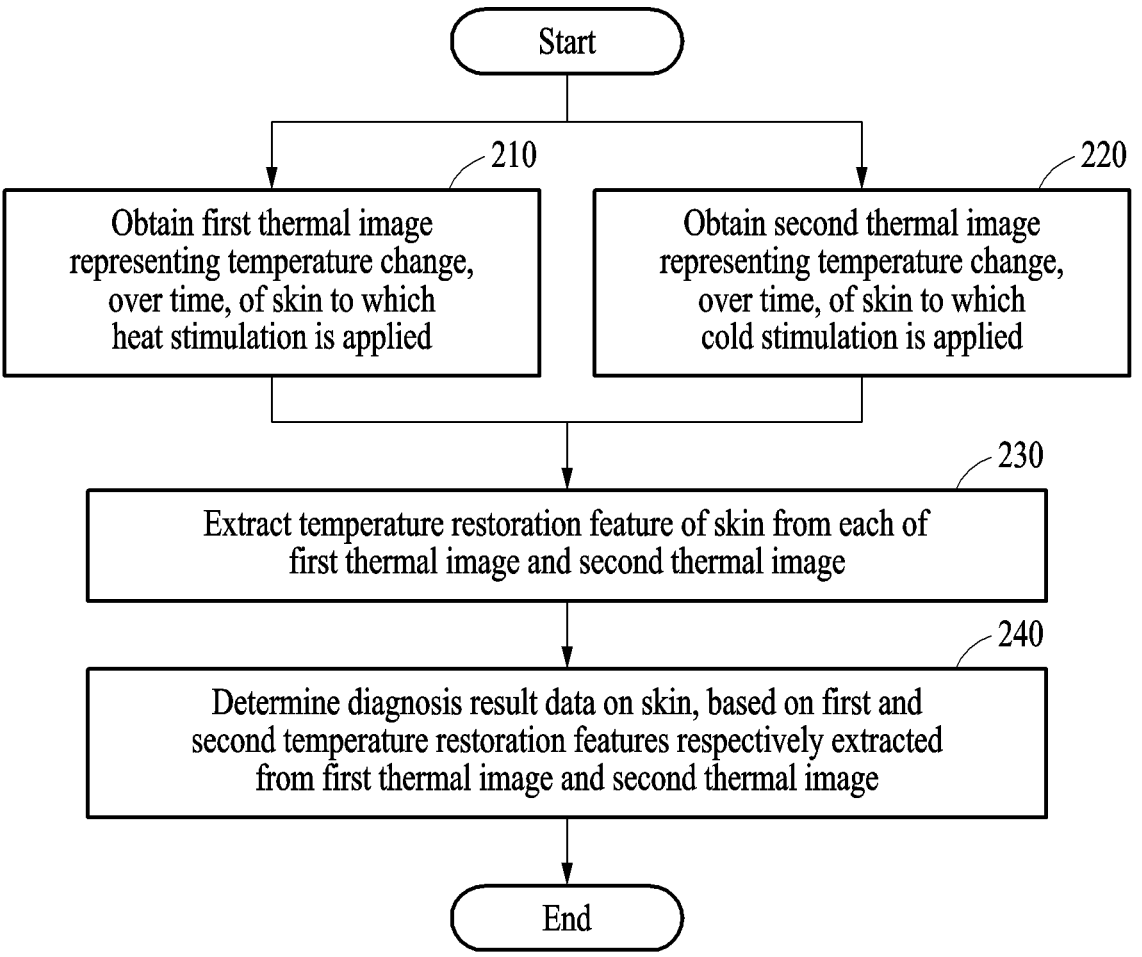
FIG. 2 is a flowchart illustrating a method of determining diagnosis result data, according to an example embodiment.

FIG. 2 is a flowchart illustrating a method of determining diagnosis result data, according to an example embodiment.

Referring to FIG. 2, in operation 210, a thermal image obtainer may obtain a first thermal image representing a temperature change, over time, of skin to which heat stimulation is applied. In addition, in operation 220, the thermal image obtainer may obtain a second thermal image representing a temperature change, over time, of the skin to which cold stimulation is applied. In this case, operations 210 and 220 may be performed in parallel or sequentially according to example embodiments. When operations 210 and 220 are sequentially performed, a performing order may be operations 210 and 220 in sequence or operations 220 and 210 in sequence.

In an example embodiment, the thermal image obtainer may apply heat stimulation and cold stimulation to the skin of a diagnosis target through a probe. For example, heat stimulation at 40 degrees Celsius and cold stimulation at 5 degrees Celsius, as an external stimulus, may be applied to the skin of the diagnosis target through the probe.

In operation 230, the thermal image obtainer may extract a temperature restoration feature of the skin from each of the first thermal image and the second thermal image. In an example embodiment, the thermal image obtainer may calculate temperature change rate values by each image frame from the first thermal image and determine an average value of the temperature change rate values to be a first temperature restoration feature. In addition, the thermal image obtainer may calculate temperature change rate values by each image frame from the second thermal image and determine an average value of the temperature change rate values to be a second temperature restoration feature.

In operation 240, the thermal image obtainer may determine diagnosis result data on the skin, based on the first and second temperature restoration features respectively extracted from the first thermal image and the second thermal image. In an example embodiment, when a temperature restoration feature is greater than or equal to a threshold value, the thermal image obtainer may determine the diagnosis target related to the skin to have an abnormality (i.e., have a lesion that is not normal). For example, the thermal image obtainer may determine the diagnosis target to have a malignant lesion. In another example embodiment, when the temperature restoration feature is greater than or equal to a threshold value, the thermal image obtainer may determine the diagnosis target related to the skin to have a vascular disease.

For example, the threshold value for determining the diagnosis target related to the skin, based on the first temperature restoration feature extracted from the first thermal image, to have an abnormality may be 0.6. In another example, the threshold value for determining the diagnosis target related to the skin, based on the second temperature restoration feature extracted from the second thermal image, to have an abnormality may be 0.4. Therefore, the threshold value for determining the diagnosis result data on the skin, based on the first temperature restoration feature, and the threshold value for determining the diagnosis result data on the skin, based on the second temperature restoration feature, may have different values.

Figure 3:
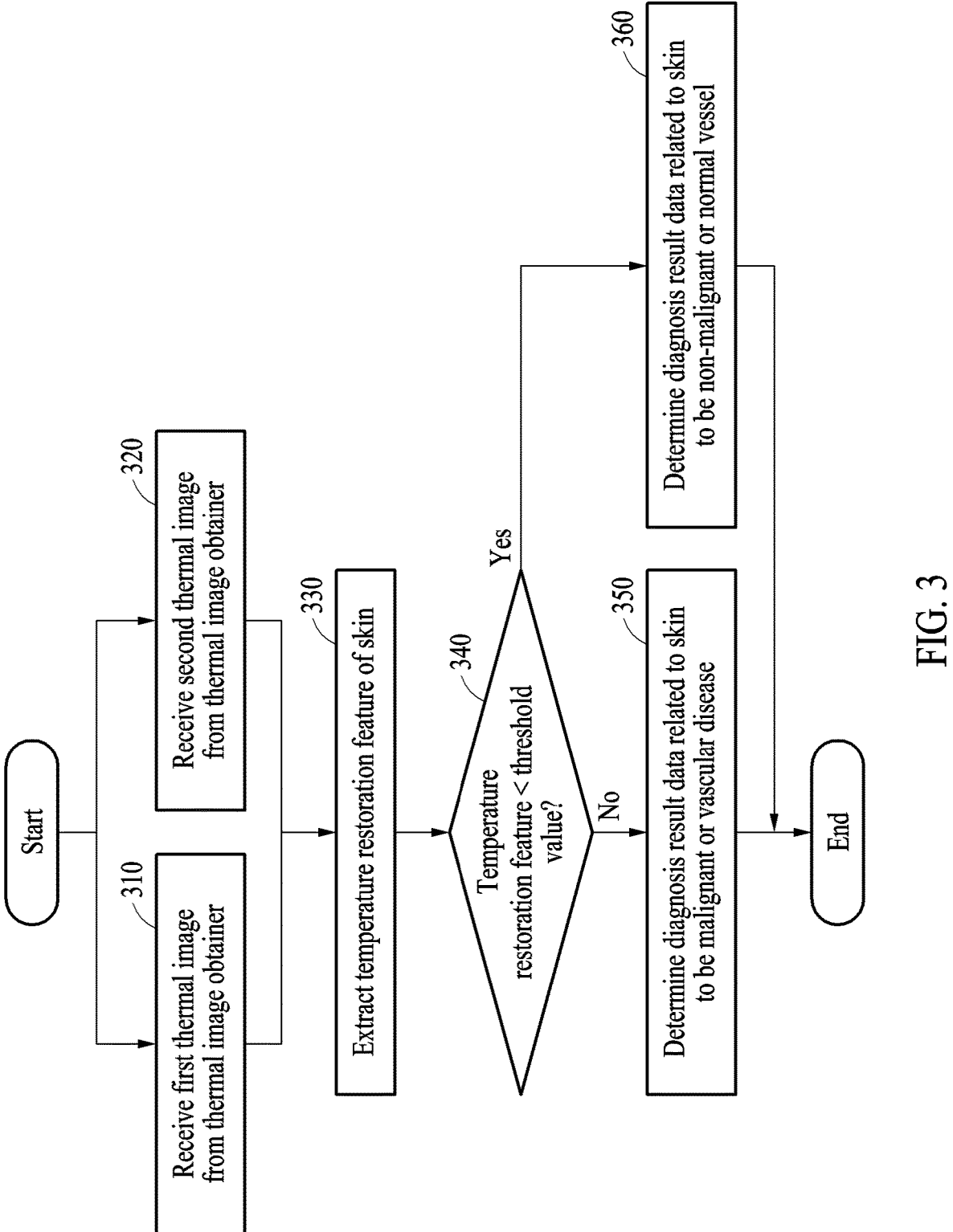
FIG. 3 is a flowchart illustrating a process of determining diagnosis result data by a device for determining diagnosis result data, according to an example embodiment.

FIG. 3 is a flowchart illustrating a process of determining diagnosis result data by a device for determining diagnosis result data, according to an example embodiment.

In an example embodiment, a device for determining diagnosis result data may correspond to a diagnosis result data determiner included in a thermal image obtainer. The device for determining diagnosis result data may be inside or outside the thermal image obtainer according to example embodiments.

Referring to FIG. 3, in operation 310, the device for determining diagnosis result data may receive a first thermal image from the thermal image obtainer. In addition, in operation 320, the device for determining diagnosis result data may receive a second thermal image from the thermal image obtainer. In this case, operations 310 and 320 may be performed in parallel or sequentially according to example embodiments. When operations 310 and 320 are sequentially performed, a performing order may be operations 310 and 320 in sequence or operations 320 and 310 in sequence.

In operation 330, the device for determining diagnosis result data may extract a temperature restoration feature of skin, based on the first thermal image and the second thermal image. The device for determining diagnosis result data may extract a first temperature restoration feature from the first thermal image and extract a second temperature restoration feature from the second thermal image.

The device for determining diagnosis result data may calculate temperature change rate values by each image frame from the first thermal image and determine an average value of the temperature change rate values to be the first temperature restoration feature. In addition, the device for determining diagnosis result data may calculate temperature change rate values by each image frame from the second thermal image and determine an average value of the temperature change rate values to be the second temperature restoration feature. The equation for determining the first temperature restoration feature and the second temperature restoration feature by the device for determining diagnosis result data may be as follows.

$$\Delta t = \frac{\text{temperature change}}{1 \text{ time frame}} \qquad \text{[Equation 1]}$$

$\Delta t$ denotes a temperature change rate by each image frame, temperature change denotes a temperature change, and 1 time frame denotes a time by each image frame.

$$\text{Average } \Delta t = \frac{\Delta t_1 + \Delta t_2 + \ldots \_ \Delta t_x}{x} \qquad \text{[Equation 2]}$$

An average value of temperature change rate values calculated through Equation 2 may be determined to be a temperature restoration feature.

In operation 340, the device for determining diagnosis result data may compare the first temperature restoration feature and the second temperature restoration feature with a threshold value corresponding to each of the first temperature restoration feature and the second temperature restoration feature. In other words, the device for determining diagnosis result data may compare the first temperature restoration feature with the threshold value corresponding to the first temperature restoration feature. In addition, the device for determining diagnosis result data may compare the second temperature restoration feature with the threshold value corresponding to the second temperature restoration feature.

When the first or second temperature restoration feature is greater than or equal to the threshold value corresponding to the first or second temperature restoration feature, in operation 350, the device for determining diagnosis result data may determine diagnosis result data related to skin to be a malignant or vascular disease and determine a diagnosis target related to the skin to have the malignant or vascular disease.

When the first or second temperature restoration feature is less than the threshold value corresponding to the first or second temperature restoration feature, in operation 360, the device for determining diagnosis result data may determine the diagnosis result data related to the skin to be a non-malignant or normal vessel and determine the diagnosis target related to the skin to have the non-malignant or normal vessel.

Figure 4A:
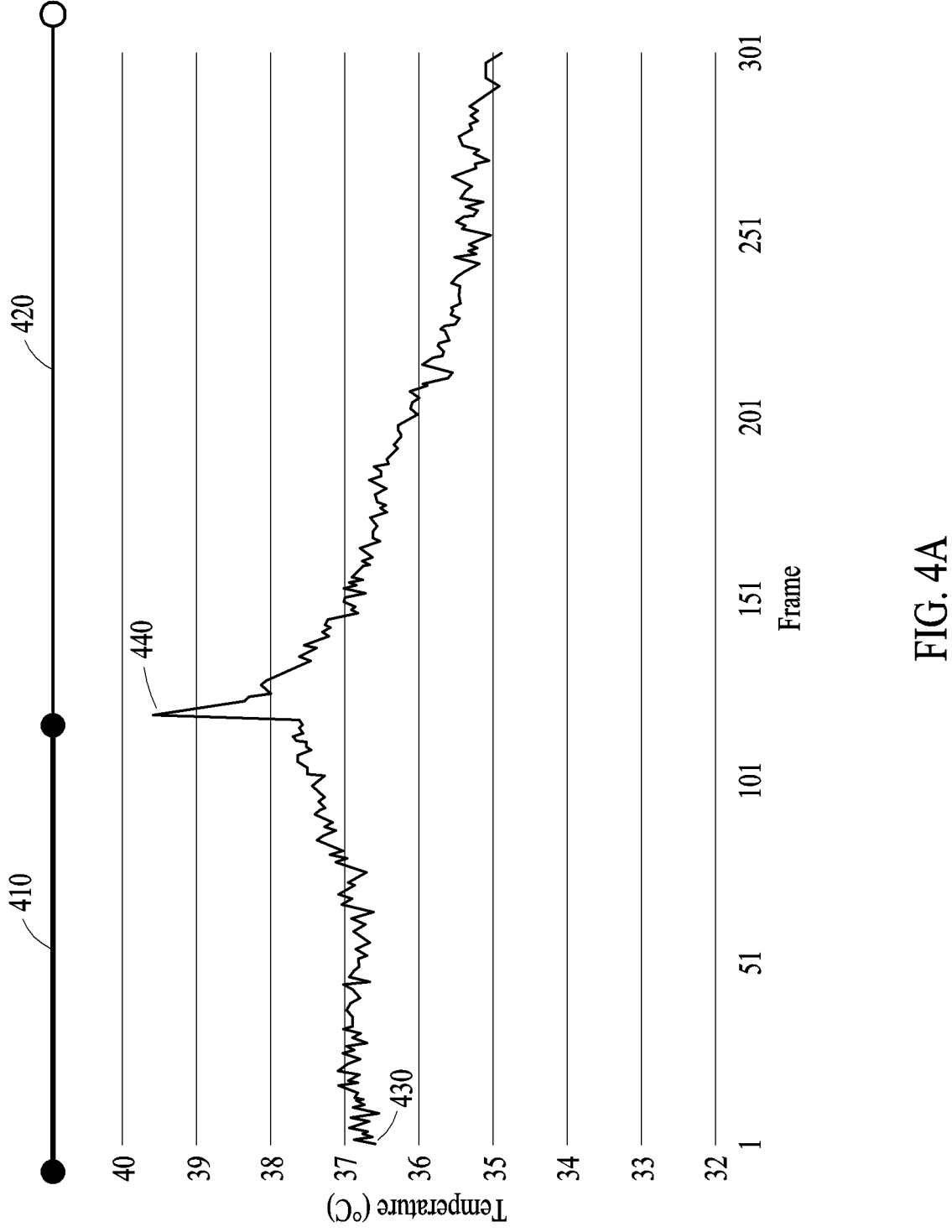
FIGS. 4A and 4B are diagrams each illustrating a temperature change of skin, according to an example embodiment.
Figure 4B:
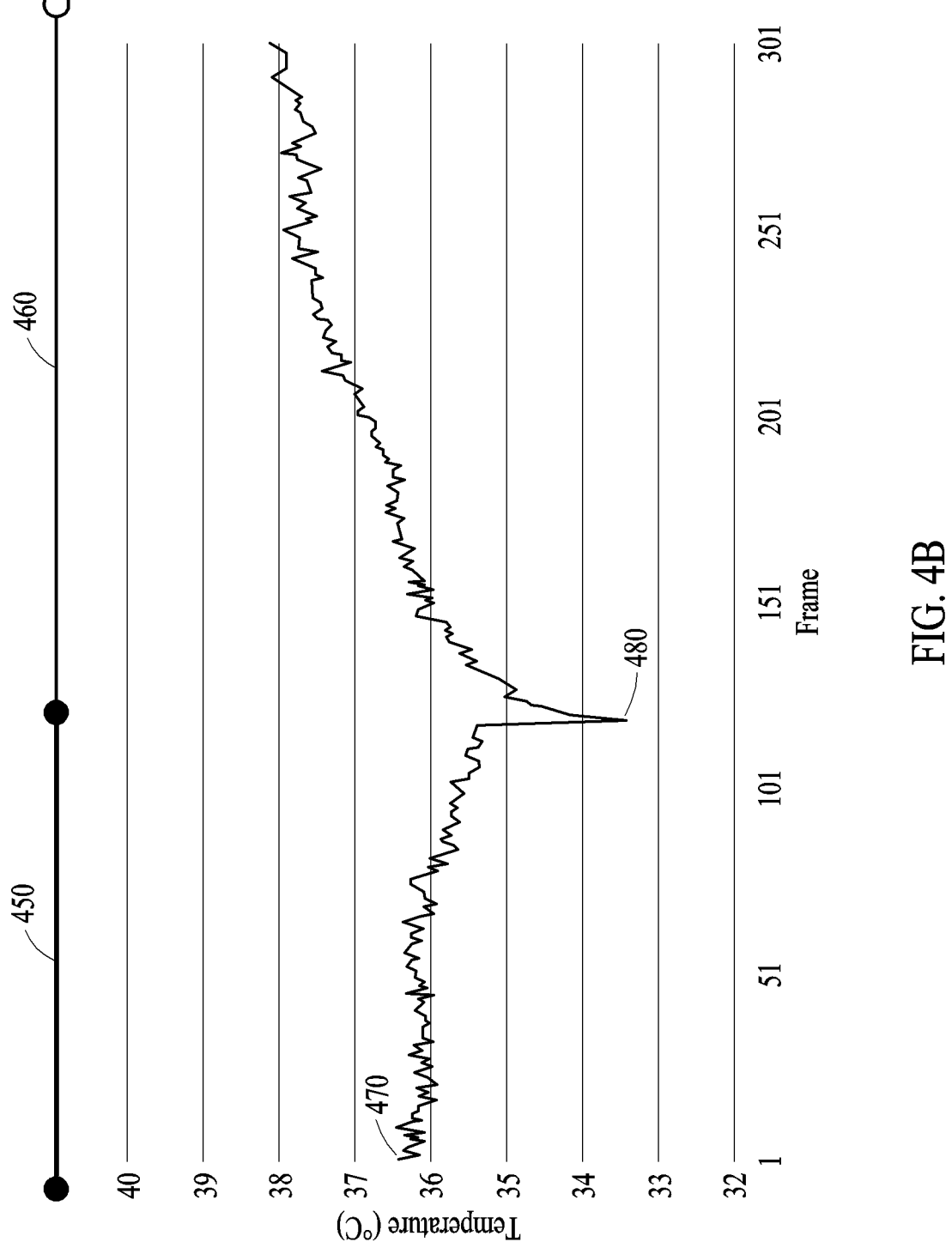

FIGS. 4A and 4B are diagrams each illustrating a temperature change of skin, according to an example embodiment.

FIG. 4A illustrates a temperature change of skin to which heat stimulation is applied. Referring to FIG. 4A, a skin temperature may be measured based on an image frame. An interval 410 may refer to an interval during which heat stimulation is applied to the skin through a probe. An interval 420 may refer to an interval during which heat stimulation is no longer applied to the skin and analysis on a temperature change of the skin is performed. In this case, the heat stimulation may be, for example, heat stimulation at about 40 degrees Celsius. In addition, the interval 410 may be about 2 minutes and the interval 420 may be about 5 minutes.

A temperature 430 may refer to a skin temperature before heat stimulation is applied to the skin. The skin temperature gradually increases when the heat stimulation starts to be applied to the skin. A temperature 440 may refer to a skin temperature when heat stimulation stops being applied to the skin. From when the heat stimulation stops being applied, a temperature of the skin to which the heat stimulation is applied may be lower than the temperature 440. A temperature change rate value of skin by each image frame may refer to a gradient between a skin temperature in a current frame and a skin temperature in the next frame. In the interval 420, a device for obtaining a thermal image or a device for determining diagnosis result data may calculate an average of temperature change rate values calculated by each image frame and determine the calculated average to be a first temperature restoration feature. The device for obtaining a thermal image or the device for determining diagnosis result data may calculate the severity of a disease, based on the first temperature restoration feature, according to example embodiments.

FIG. 4B illustrates a temperature change of skin to which cold stimulation is applied. Referring to FIG. 4B, a skin temperature may be measured based on an image frame. An interval 450 may refer to an interval during which cold stimulation is applied to the skin through a probe. An interval 460 may refer to an interval during which cold stimulation is no longer applied to the skin and analysis on a temperature change of the skin is performed. In this case, the cold stimulation may be, for example, cold stimulation at about 5 degrees Celsius. In addition, the interval 450 may be about 2 minutes and the interval 460 may be about 5 minutes.

A temperature 470 may refer to a skin temperature before cold stimulation is applied to the skin. The skin temperature gradually decreases when the cold stimulation starts to be applied to the skin. A temperature 480 may refer to a skin temperature when cold stimulation stops being applied to the skin. From when the cold stimulation stops being applied, a temperature of the skin to which the cold stimulation is applied may be higher than the temperature 480. A temperature change rate value of skin by each image frame may refer to a gradient between a skin temperature in a current frame and a skin temperature in the next frame. In the interval 460, a device for obtaining a thermal image or a device for determining diagnosis result data may calculate an average of temperature change rate values calculated by each image frame and determine the calculated average to be a second temperature restoration feature. The device for obtaining a thermal image or the device for determining diagnosis result data may calculate the severity of a disease, based on the second temperature restoration feature, according to example embodiments.

Figure 5:
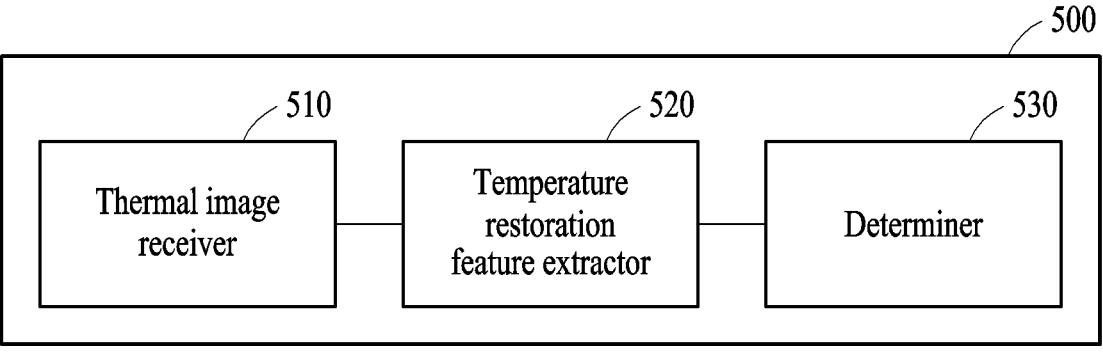
FIG. 5 is a diagram illustrating a configuration of a device for determining diagnosis result data, according to an example embodiment.

FIG. 5 is a diagram illustrating a configuration of a device for determining diagnosis result data, according to an example embodiment.

Referring to FIG. 5, a device 500 for determining diagnosis result data may correspond to a diagnosis result data determiner and a device for determining diagnosis result data described herein.

In an example embodiment, the device 500 for determining diagnosis result data may include a thermal image receiver 510, a temperature restoration feature extractor 520, and a determiner 530. The thermal image receiver 510 may receive a first thermal image and a second thermal image from a device for obtaining a thermal image. The temperature restoration feature extractor 520 may extract a temperature restoration feature of skin from each of the first thermal image and the second thermal image. In addition, the temperature restoration feature extractor 520 may calculate temperature change rate values by each image frame from the first thermal image and determine an average value of the temperature change rate values to be a first temperature restoration feature and may calculate temperature change rate values by each image frame from the second thermal image and determine an average value of the temperature change rate values to be a second temperature restoration feature.

The determiner 530 may determine diagnosis result data on skin, based on the first temperature restoration feature extracted from the first thermal image and the second temperature restoration feature extracted from the second thermal image. The determiner 530 may determine a diagnosis target related to the skin to have an abnormality or have a vascular disease when the first or second temperature restoration feature is greater than or equal to a threshold value.

The units described herein may be implemented using a hardware component, a software component and/or a combination thereof. A processing device may be implemented using one or more general-purpose or special-purpose computers, such as, for example, a processor, a controller and an arithmetic logic unit (ALU), a DSP, a microcomputer, an FPGA, a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or uniformly instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs or DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher-level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. A method of determining diagnosis result data by using a thermal image, the method comprising:
   obtaining a first thermal image representing a temperature change, over time, of skin to which heat stimulation is applied;
   obtaining a second thermal image representing a temperature change, over time, of skin to which cold stimulation is applied;
   extracting a temperature restoration feature of the skin from each of the first thermal image and the second thermal image by:
   calculating temperature change rate values by each image frame from the first thermal image and determining an average value of the temperature change rate values to be a first temperature restoration feature;
   calculating temperature change rate values by each image frame from the second thermal image and determining an average value of the temperature change rate values to be a second temperature restoration feature; and
   determining diagnosis result data related to the skin, based on a comparison of the first temperature restoration feature to a first threshold value and the second temperature restoration feature to a second corresponding threshold value, wherein the first threshold value is greater than the second threshold value, wherein the diagnosis result data indicates a presence of an abnormality when the first or second temperature restoration feature is greater than or equal to its corresponding threshold value,
   wherein the temperature change rate values equate to a difference in temperature between two sequential image frames divided by a time difference between the sequential image frames.

2. The method of claim 1, wherein the abnormality is a malignant lesion.

3. The method of claim 1, wherein the abnormality is vascular disease.

4. A non-transitory computer-readable storage medium storing instructions that, when executed by a processor, cause the processor to perform the method of claim 1.

5. The method of claim 1, wherein the heat stimulation is applied with a first heat stimulation probe and the cold stimulation is applied with a second cold stimulation probe separate from the first heat stimulation probe, wherein the heat stimulation and the cold stimulation are applied in parallel.

6. A device for obtaining a thermal image for determining diagnosis result data, the device comprising:
   a temperature controller for transmitting, to a probe, a control signal for applying heat stimulation and cold stimulation to skin;
   the probe for applying heat stimulation and cold stimulation to skin, based on the control signal of the temperature controller;
   an infrared camera for obtaining a first thermal image from skin to which heat stimulation is applied by the probe and for obtaining a second thermal image from skin to which cold stimulation is applied by the probe;
   a temperature restoration feature extractor for extracting a temperature restoration feature of skin from each of the first thermal image and the second thermal image by:
   calculating temperature change rate values by each image frame from the first thermal image and determining an average value of the temperature change rate values to be a first temperature restoration feature;
   calculating temperature change rate values by each image frame from the second thermal image and determining an average value of the temperature change rate values to be a second temperature restoration feature; and
   a diagnosis result data determiner for determining diagnosis result data, based on a comparison of the first temperature restoration feature to a first threshold value and the second temperature restoration feature to a second corresponding threshold value, wherein the first threshold value is greater than the second threshold value, wherein the diagnosis result data indicates a presence of an abnormality when the first or second temperature restoration feature is greater than or equal to its corresponding threshold value, wherein the temperature change rate values equate to a difference in temperature between two sequential image frames divided by a time difference between the sequential image frames.

7. The device of claim 6, further comprising:

a first heat stimulation probe to apply the heat stimulation; and a second cold stimulation probe to apply the cold stimulation, wherein the second cold stimulation probe is separate from the first heat stimulation probe, wherein the heat stimulation and the cold stimulation are applied in parallel.

8. A device for determining diagnosis result data by using a thermal image, the device comprising:

a thermal image receiver for receiving the first thermal image and the second thermal image from an infrared camera;

a temperature restoration feature extractor for extracting a temperature restoration feature of skin from each of the first thermal image and the second thermal image by:

calculating temperature change rate values by each image frame from the first thermal image and determining an average value of the temperature change rate values to be a first temperature restoration feature;

calculating temperature change rate values by each image frame from the second thermal image and determining an average value of the temperature change rate values to be a second temperature restoration feature; and a determiner for determining diagnosis result data related to the skin, based on a comparison of the first temperature restoration feature to a first threshold value and the second temperature restoration feature to a second corresponding threshold value, wherein the first threshold value is greater than the second threshold value, wherein the diagnosis result data indicates a presence of an abnormality when the first or second temperature restoration feature is greater than or equal to its corresponding threshold value, wherein the temperature change rate values equate to a difference in temperature between two sequential image frames divided by a time difference between the sequential image frames.

9. The device of claim 8, wherein the abnormality is a malignant lesion.

10. The device of claim 8, wherein the abnormality is vascular disease.

11. The device of claim 8, further comprising:

a first heat stimulation probe to apply heat stimulation; and a second cold stimulation probe to apply cold stimulation, wherein the second cold stimulation probe is separate from the first heat stimulation probe, wherein the heat stimulation and the cold stimulation are applied in parallel.

* * * * *